US012702543B2

(12) United States Patent
Skarsgard et al.

(10) Patent No.: US 12,702,543 B2
(45) Date of Patent: Aug. 11, 2026

(54) TISSUE ANCHORS

(71) Applicant: VESALIUS CARDIOVASCULAR INC., Vancouver (CA)

(72) Inventors: Peter Lloyd Skarsgard, Vancouver (CA); Ryan Harrington, Vancouver (CA); Andrew Meyer, Vancouver (CA)

(73) Assignee: VESALIUS CARDIOVASCULAR INC., Vancouver (CA)

( * ) Notice: Subject to any disclaimer, the term of this patent is extended or adjusted under 35 U.S.C. 154(b) by 0 days.

(21) Appl. No.: 18/676,663

(22) Filed: May 29, 2024

(65) Prior Publication Data

US 2025/0366985 A1 Dec. 4, 2025

(51) Int. Cl.
*A61F 2/24* (2006.01)

(52) U.S. Cl.
CPC ........ *A61F 2/24* (2013.01); *A61F 2220/0008* (2013.01)

(58) Field of Classification Search
CPC ........ A61F 2/24; A61F 2/2418; A61F 2/2427; A61F 2002/30482; A61F 2002/30481; A61F 2002/30479; A61F 2002/30477; A61F 2/2454; A61B 2017/0445; A61B 2017/0443; A61B 2017/0441; A61B 2017/0424; A61B 2017/0422; A61B 17/0401; A61B 2017/0412
See application file for complete search history.

(56) References Cited

U.S. PATENT DOCUMENTS

| | | | | |
|---|---|---|---|---|
| 5,100,417 | A * | 3/1992 | Cerier | A61B 17/0401 606/232 |
| 10,357,640 | B2 * | 7/2019 | Abbate | A61F 5/08 |
| 2003/0088272 | A1 * | 5/2003 | Smith | A61B 17/0401 606/232 |
| 2004/0044350 | A1 | 3/2004 | Martin et al. | |
| 2004/0049262 | A1 | 3/2004 | Obermiller et al. | |
| 2004/0138707 | A1 * | 7/2004 | Greenhalgh | A61B 17/68 606/232 |
| 2004/0143323 | A1 | 7/2004 | Chawla | |
| 2005/0075727 | A1 | 4/2005 | Wheatley | |
| 2006/0178700 | A1 | 8/2006 | Quinn | |
| 2007/0005069 | A1 * | 1/2007 | Contiliano | A61B 17/0401 606/304 |

(Continued)

FOREIGN PATENT DOCUMENTS

| | | | |
|---|---|---|---|
| EP | 3028668 | A1 | 6/2016 |
| JP | 2009522066 | A * | 6/2009 |

(Continued)

OTHER PUBLICATIONS

Translation of JP2009522066A. (Year: 2009).*

*Primary Examiner* — Christie Bahena
(74) *Attorney, Agent, or Firm* — Oyen Wiggs Green & Mutala LLP

(57) ABSTRACT

A tissue anchor is disclosed. The tissue anchor comprises a base and first, second, third and fourth prongs being joined to the base at proximal ends thereof. In some embodiments, each of the first, second, third and fourth prongs extends radially outwardly from the proximal end along an arcuate path towards a distal end. The first, second, third and fourth prongs may be radially symmetrically such that the anchor has radial symmetry about a central axis of the anchor.

12 Claims, 3 Drawing Sheets

(56) References Cited

U.S. PATENT DOCUMENTS

2007/0112425 A1 5/2007 Schaller et al.
2007/0270943 A1 11/2007 Solem et al.
2007/0282429 A1* 12/2007 Hauser .................. A61F 2/2466 623/1.36
2008/0086164 A1 4/2008 Rowe
2008/0125861 A1 5/2008 Webler et al.
2008/0195126 A1 8/2008 Solem
2009/0240326 A1 9/2009 Wilson et al.
2010/0023117 A1 1/2010 Yoganathan et al.
2010/0082094 A1 4/2010 Quadri et al.
2011/0071626 A1 3/2011 Wright et al.
2012/0290077 A1 11/2012 Aklog et al.
2013/0172978 A1 7/2013 Vidlund et al.
2014/0142689 A1 5/2014 De Canniere et al.
2014/0358224 A1 12/2014 Tegels et al.
2015/0057705 A1* 2/2015 Vidlund .................... A61F 2/24 606/228
2017/0065418 A1 3/2017 Skarsgard
2017/0216023 A1 8/2017 Lane et al.
2017/0258589 A1 9/2017 Pham et al.
2018/0049871 A1 2/2018 Zeng et al.
2018/0071098 A1 3/2018 Alon
2018/0289474 A1 10/2018 Rajagopal et al.
2018/0289480 A1 10/2018 D'Ambra et al.
2018/0289483 A1 10/2018 Speziali et al.
2019/0343626 A1* 11/2019 Smirnov ............... A61F 2/2466
2019/0343634 A1* 11/2019 Garvin ............... A61B 17/0401
2020/0085443 A1* 3/2020 Miller ................ A61B 17/1285
2023/0136876 A1* 5/2023 Herbst .................. A61F 2/0805 606/232

FOREIGN PATENT DOCUMENTS

WO 2011072084 A2 6/2011
WO 2013028387 A2 2/2013
WO WO-2014045165 A1 * 3/2014 ......... A61B 17/0401
WO 2015152980 A1 10/2015
WO 2016209970 A1 12/2016
WO 2018057716 A1 3/2018
WO WO-2022094407 A1 * 5/2022 ......... A61B 17/0401

* cited by examiner

TISSUE ANCHORS

FIELD OF THE INVENTION

The invention pertains to tissue anchors, and in particular, those for implanting into the heart of a subject.

BACKGROUND OF THE INVENTION

Tissue anchors are known in the art. Tissue anchors that are resistant to extraction by a force of unpredictable direction are required. There is a need for an improved tissue anchors, in particular those for repairing heart valves without involving open heart procedures.

SUMMARY

One aspect of the invention provides a tissue anchor. The tissue anchor comprises a base and first, second, third and fourth prongs being joined to the base at proximal ends thereof. In some embodiments, each of the first, second, third and fourth prongs extends radially outwardly from the proximal end along an arcuate path towards a distal end. The first, second, third and fourth prongs may be radially symmetrically such that the anchor has radial symmetry about a central axis of the anchor.

In one example embodiment, the tissue anchors are delivered to the papillary muscles, for use in securing a device, such as a replacement heart valve, to the papillary muscle or ventricular myocardium.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Figure 1:
FIG. 1 is a perspective view illustrating a tissue anchor according to an example embodiment of the invention.
Figure 1:
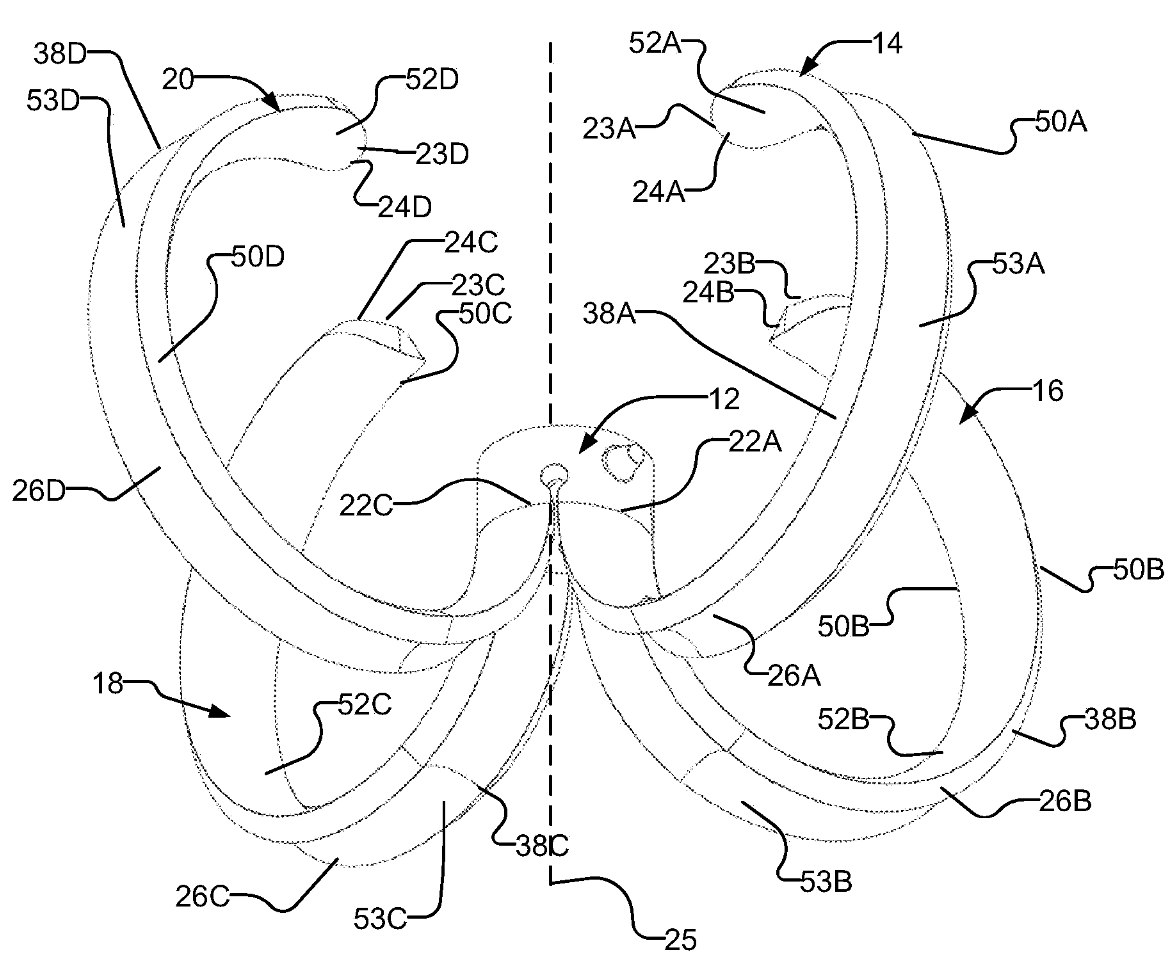
Figure 2:
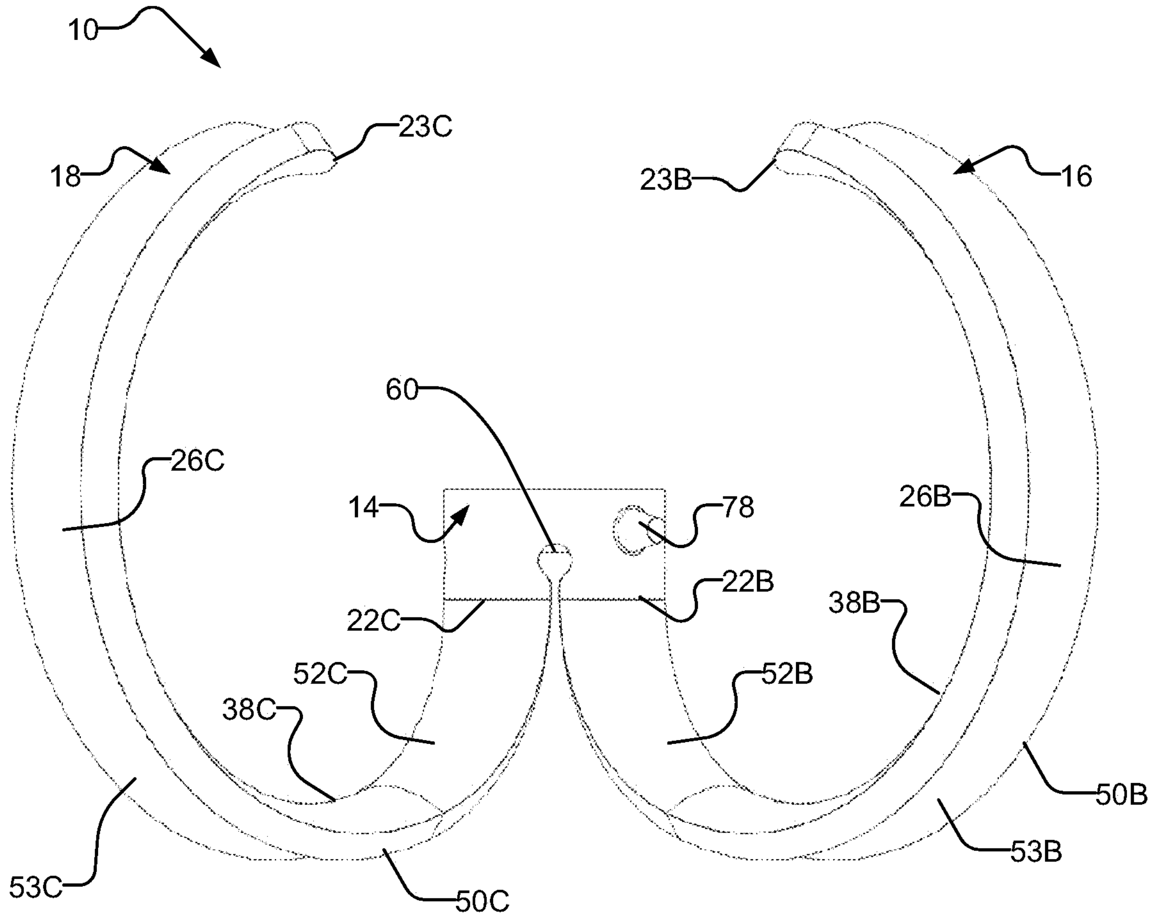
FIG. 2 is a front view of the FIG. 1 tissue anchor.
Figure 3:
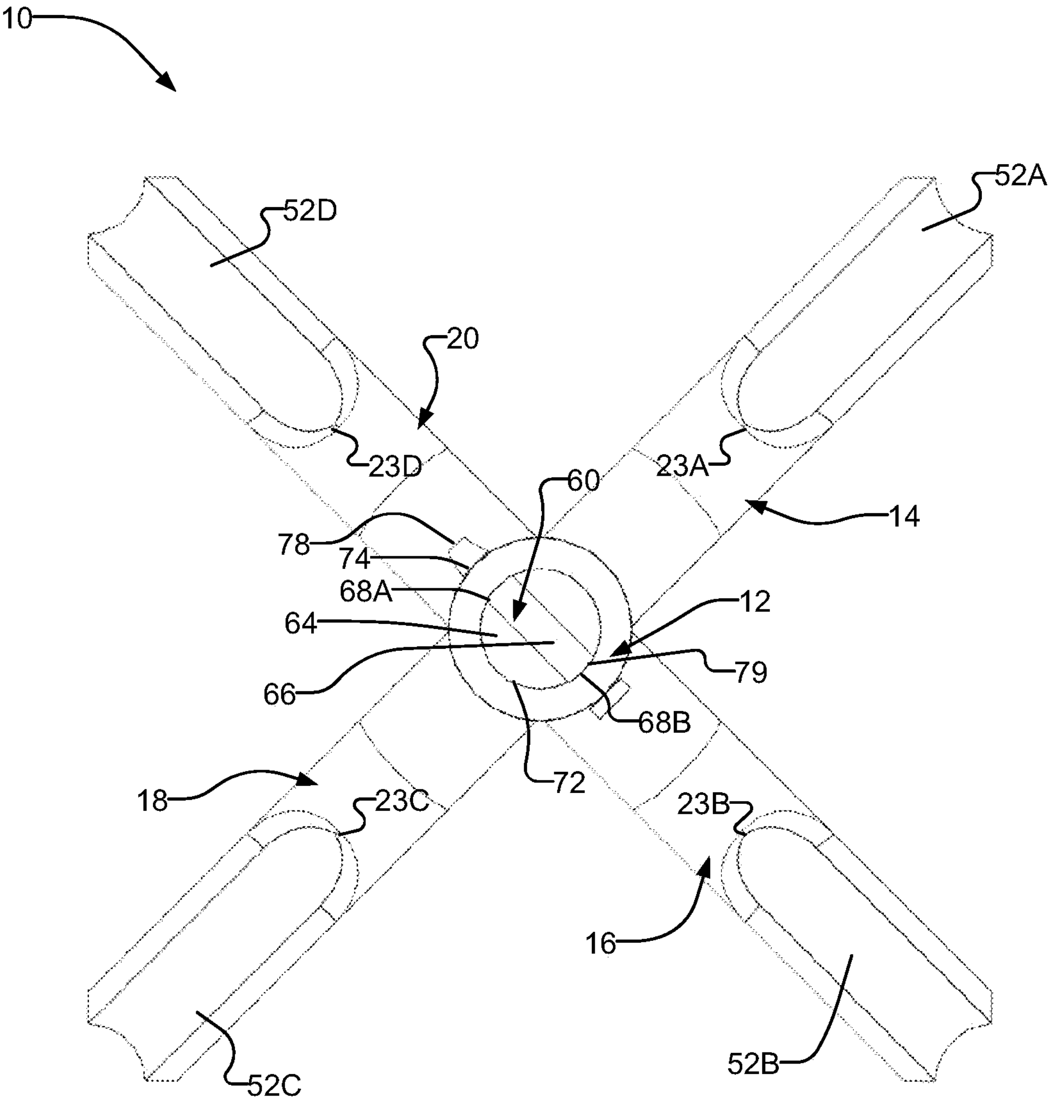
FIG. 3 is a top view of the FIG. 1 tissue anchor.

Referring to FIGS. 1-3, an embodiment of the invention is a tissue anchor 10. In some embodiments, the anchor 10 comprises a base 12, a first prong 14, a second prong 16, a third prong 18, and a fourth prong 20. Each of the prongs 14, 16, 18, 20 comprise a proximal end 22A,B,C,D joined to the base, extending outwardly to a respective distal end 24A, B,C,D. In some embodiments, the prongs 14, 16, 18, 20 terminate in a respective distal tip 23A,B,C,D. In some example embodiments, the distal tip 23A,B,C,D comprises a rounded or arcuate edge.

In the illustrated embodiments, the anchor 10 comprises four prongs; however, this is not mandatory. The anchor 10 may comprise any suitable number of prongs. In some embodiments, the anchor 10 comprises an even number of prongs, including but not limited to 2, 4, 6, 8, etc. The prongs may be arranged such that the anchor 10 has radial symmetry about a central axis 25 of the anchor 10. The central axis 25 of the anchor 10 may be aligned with the central axis of the base 12.

In some embodiments, the prongs 14, 16, 18, 20 are arranged to extend radially outwardly with respect to the central axis 25 of the anchor 10. In some embodiments, the prongs 14, 16, 18, 20 are arranged radially spaced-apart. In some embodiments, the prongs 14, 16, 18, 20 are arranged such that the circumferential spacing between adjacently positioned prongs 14, 16, 18, 20 is equal or substantially equal. In some embodiments, the prongs 14, 16, 18, 20 may be arranged with equal or substantially equal angular and/or radial spacing around the central axis 25.

In some embodiments, the first and third prongs 14, 18 are arranged to extend radially outwardly in opposing directions. In some embodiments, the second and fourth 16, 20 prongs are arranged to extend radially outwardly in opposing directions. The prongs may be arranged such that the anchor 10 has radial symmetry about the central axis 25 of the anchor 10. In such embodiments, the distal tips 23A,C of the first and third prongs 14, 18 are arranged to face each other, and the distal tips 23B,D of the second and fourth prongs 16, 20 are arranged to face each other.

In some embodiments, each of the prongs 14, 16, 18, 20 extend from the proximal end 22A,B,C,D along a respective arcuate path 26A,B,C,D towards the respective distal end 24A,B,C,D.

The arc measure of each of prongs 14, 16, 18, 20 may be greater than 180°, and in some embodiments, between about 180° and about 320°, and in some embodiments, between about 200° and about 270°. As used herein, the arc measure is the degree measure of the central angle, whose vertex is at the center of the circle, that intercepts the arc. The arc is formed by each of the prongs. The two sides of a central angle are radii that intercept the circle at the opposite ends of an arc. For example, the arc measure of a full circle is 360°, and the arc measure of a semi-circle is 180°.

In some embodiments, the base 12 is located at the geometric center of the anchor 10. In such embodiments, the distance between the base 12 and each of the tips 23A,B,C,D of the respective prongs 14, 16, 18, 20 is equal or substantially equal. In some embodiments, each of the prongs 14, 16, 18, 20 extend from the base 12 at the respective proximal ends 22A,B,C,D thereof. The base 12 is a location shared by all of the prongs 14, 16, 18, 20. In such embodiments, the prongs 14, 16, 18, 20 are each joined at the base 12 at the respective proximal ends 22A,B,C,D. In some embodiments, the arc measure of the prongs 14, 16, 18, 20 measured at the proximal ends 22A,B,C,D is 0°, or approximately 0°. As used herein, "approximately" means +/−10°.

In some embodiments, the radii of curvature as defined by a distance between a point along the respective arcuate paths 26A,B,C,D, and the respective center of curvature of the respective prong 14, 16, 18, 20 is the same or substantially the same to each other. The radii of curvature defined by the arcuate paths 26A, B, C, D of the first, second, third and fourth prongs 14, 16, 18, 20 may however be different from each other. In some embodiments, two or more of the radii of curvature may be the same or substantially the same to each other, and the other one or more of the radii of curvature may be different. As used herein, the "center of curvature" is a center of a circle.

In some embodiments, the prongs 14, 16, 18, 20 comprise a curved surface on inner and/or outer faces 52A,B,C,D, 53A,B,C,D of the prongs 14, 16, 18, 20. In some embodiments, one of the faces 52A,B,C,D, 53A,B,C,D of the prongs 14, 16, 18, 20 comprise a concave curved surface, and the other one of the faces 52A,B,C,D, 53A,B,C,D of the prongs 14, 16, 18, 20 comprise a convex curved surface. In some embodiments, the inner face 52A,B,C,D of the prongs 14, 16, 18, 20 comprise a convex curved surface, and the outer face 53A,B,C,D of the prongs 14, 16, 18, 20 comprise a concaved curved surface. The inner face 52A,B,C,D of the prongs 14, 16, 18, 20 faces the center of curvature, while the opposing outer face 53A,B,C,D faces away from the center of curvature.

In some embodiments, the prongs 14, 16, 18, 20 extend along a width thereof along the inner and outer faces 52A,B,C,D, 53A,B,C,D, from a respective first edge 38A, B,C,D towards an opposing respective second edge 50A,B, C,D.

In some embodiments, an attachment point 60 is arranged at the base 12. In some embodiments, the attachment point 60 is at the geometric center of the anchor 10. In some embodiments, at least a region of the attachment point 60 is arranged to coincide with, or substantially coincide with the central axis 25 of the anchor 10. The attachment point 60 is positioned for securing a tether to the anchor 10. In some embodiments, a channel 64 is defined within the base 12. In some embodiments, the attachment point 60 comprises a pin 66. The pin 66 may be arranged to extend within the channel 64 across the base 12, from a first point 68A to a second point 68B on an inner wall 72 of the base 12.

The pin 66 may be arranged to pass through the central axis 25 of the anchor 10 as the pin 66 extends from the first to the second point 68A,B. The pin 66 may be secured to the first and second points 68A,B. In some embodiments, the first point 68A is positioned diametrically opposed to the second point 68B, but this is not mandatory. The first and second points 68A, B may be positioned at any suitable positions on the inner wall 72 of the base. In an example use embodiments, a tether is secured to the pin 66 by forming a closed loop and securing the closed loop around the pin 66.

In some embodiments, the pin 66 is arranged to protrude outwardly through an outer wall 74 of the base. In some embodiments, one end 78 of the pin 66 extends outwardly from the outer wall 74 of the base 14, passing through the first point 68A, and therefrom extends longitudinally to the second point 68B along the inner wall 72 of the base 14. In some embodiments, the opposite end 79 of the pin 66 is joined to the second point 68B of the inner wall 72 of the base 14.

In some example use embodiments, the one end 78 of the pin 66 is dimensioned for insertion into a slot of a needle or other delivery devices, configured to deliver the anchor 10 to a desired implantation location within a heart of a subject. In an example use embodiment, the anchors 10 are delivered to the papillary muscle or ventricular myocardium, for use in securing a device, such as a replacement heart valve.

The anchor 10 described herein is shaped and dimensioned to allow the anchor to resist extraction equally on the surfaces thereof, independent of the direction of the extraction force exerted by pulling the tether that is secured to the attachment point 60. The anchor 10 as described may comprise a base 12 being positioned at the geometric center of the radially symmetrical anchor 10. The attachment point 60 for the tether may also be positioned at the geometric center of the anchor 10. This specific position of the base relative to the prongs 14, 16, 18, 20 advantageously prevents a moment of torque when the anchor is being pulled by the tether. Safe and consistent resistance to an extraction force on the anchors in any direction after implantation is important since it is not possible to predict the direction of a force of anchor extraction before implantation.

Throughout the foregoing description and the drawings, in which corresponding and like parts are identified by the same reference characters, specific details have been set forth in order to provide a more thorough understanding to persons skilled in the art. However, well known elements may not have been shown or described in detail or at all to avoid unnecessarily obscuring the disclosure.

As will be apparent to those skilled in the art in the light of the foregoing disclosure, many alterations and modifications are possible in the practice of this invention without departing from the scope thereof. Accordingly, the description and drawings are to be regarded in an illustrative, rather than a restrictive, sense.

The invention claimed is:

1. A tissue anchor comprising:

a base having a substantially flat bottom end, wherein the base is positioned at a geometric center of the tissue anchor;

first, second, third and fourth prongs being joined to the base at proximal ends thereof, each of the first, second, third and fourth prongs extending radially outwardly from the proximal end along an arcuate path towards a distal end, wherein the first, second, third and fourth prongs are joined to the base at a second end opposite to the flat bottom end of the base; and an attachment point extending across a channel defined within the base, the attachment point positioned between the flat bottom end and the second end of the base, the attachment point comprising a pin, arranged to extend from a first point to a second point on an inner wall of the base, wherein one end of the pin protrudes outwardly through an outer wall of the base, and wherein said one end is dimensioned for insertion into a slot of a delivery device for delivery of the tissue anchor to a desired implantation location of a tissue.

2. The tissue anchor according to claim 1, wherein the first, second, third and fourth prongs are radially symmetrically arranged such that the anchor has radial symmetry about a central axis thereof.

3. The tissue anchor according to claim 1, wherein the first and third prongs are arranged to extend radially outwardly in opposing directions, and the second and fourth prongs are arranged to extend radially outwardly in opposing directions.

4. The tissue anchor according to claim 1, wherein the first, second, third and fourth prongs each terminate in a distal tip.

5. The tissue anchor according to claim 4, wherein the distal tip is a rounded tip.

6. The tissue anchor according to claim 4, wherein the distal tips of the first and third prongs are arranged to face each other, and wherein the distal tips of the second and fourth prongs are arranged to face each other.

7. The tissue anchor according to claim 1, wherein an arc measure of the prongs is between 180° and 320°.

8. The tissue anchor according to claim 1, wherein the prongs comprise a curved surface on an inner face of the prongs and/or an opposing outer face of the prongs, and wherein the inner face of the prongs are arranged to face a center of curvature defined by the prongs.

9. The tissue anchor according to claim 8, wherein the inner face of the prongs comprises a convex curved surface.

10. The tissue anchor according to claim 8, wherein the outer face of the prongs comprises a concave curved surface.

11. The tissue anchor according to claim 1, wherein the attachment point is positioned at a geometric center of the tissue anchor.

12. The tissue anchor according to claim 1, wherein the pin comprises a first end extending longitudinally to an opposing second end, wherein the first end is joined to the first point and the second end is joined to the second point of the inner wall of the base.

* * * * *